US011529291B2

(12) United States Patent
Sazonov et al.

(10) Patent No.: US 11,529,291 B2
(45) Date of Patent: Dec. 20, 2022

(54) INSTRUMENTED INFANT FEEDING BOTTLE

(71) Applicants: The Board of Trustees of the University of Alabama, Tuscaloosa, AL (US); THE UAB RESEARCH FOUNDATION, Birmingham, AL (US)

(72) Inventors: Eduard S. Sazonov, Northport, AL (US); Ariel A. Salas, Hoover, AL (US); Paula Catherine Chandler-Laney, Birmingham, AL (US)

(73) Assignees: The Board of Trustees of the University of Alabama, Tuscaloosa, AL (US); The UAB Research Foundation, Birmingham, AL (US)

( * ) Notice: Subject to any disclaimer, the term of this patent is extended or adjusted under 35 U.S.C. 154(b) by 469 days.

(21) Appl. No.: 16/664,437

(22) Filed: Oct. 25, 2019

(65) Prior Publication Data
US 2020/0129380 A1    Apr. 30, 2020

Related U.S. Application Data

(60) Provisional application No. 62/751,069, filed on Oct. 26, 2018.

(51) Int. Cl.
*A61J 11/00* (2006.01)
*G01L 27/00* (2006.01)
*A61J 9/00* (2006.01)

(52) U.S. Cl.
CPC ............ *A61J 9/008* (2013.01); *A61J 9/001* (2013.01); *A61J 11/008* (2013.01); *G01L 27/00* (2013.01); *A61J 2200/70* (2013.01)

(58) Field of Classification Search
None
See application file for complete search history.

(56) References Cited

U.S. PATENT DOCUMENTS 3,645,262 A    2/1972   Harrigan et al.
3,895,533 A    7/1975   Steier
(Continued)

FOREIGN PATENT DOCUMENTS

CA    2614158    6/2009
EP    0094384    11/1983
(Continued)

OTHER PUBLICATIONS

"MilkSense Personal Breastfeeding Monitor", on-line at http://milksense.com/template/english/milksense-tech-en.html. 2014, 1 page.
(Continued)

*Primary Examiner* — Paul M. West
*Assistant Examiner* — Mark A Shabman
(74) *Attorney, Agent, or Firm* — Meunier Carlin & Curfman LLC (57) ABSTRACT

A feeding bottle includes a bottle enclosure defining a hollow bottle chamber, wherein the enclosure defines a feeding outlet at a first end and an attachment structure 26 at a second end. A bottom housing defines an instrument compartment extending between a closed exterior portion of the bottom housing and a separation surface within the bottom housing, wherein the bottom housing is configured for detachable connection to the attachment structure 26 of the bottle enclosure. A relief valve is positioned within the separation surface of the bottom housing. A pressure sensor is positioned adjacent the separation surface of the bottom housing and connected by a passageway to the instrument compartment in the bottom housing, wherein the pressure sensor is configured to detect changes of pressure in the bottle enclosure.

17 Claims, 7 Drawing Sheets

Fully assembled Instrumented Bottle

(56) References Cited

U.S. PATENT DOCUMENTS

| | | | |
|---|---|---|---|
| 4,280,228 | A | 7/1981 | Sulzmann |
| 4,856,663 | A | 8/1989 | Epp |
| D359,838 | S | 7/1995 | Laseinde |
| 5,827,191 | A | 10/1998 | Rosenfeld |
| 6,033,367 | A | 3/2000 | Goldfield |
| 6,109,100 | A | 8/2000 | Buckley et al. |
| 6,264,049 | B1 | 7/2001 | Shteynberg |
| 6,966,904 | B2 | 11/2005 | Ruth et al. |
| 7,111,760 | B2 | 9/2006 | Pagovich et al. |
| 7,765,613 | B2 | 8/2010 | Carr |
| 7,896,835 | B2 | 3/2011 | Dahan et al. |
| 8,114,030 | B2 | 2/2012 | Ales et al. |
| 8,151,372 | B2 | 4/2012 | Densmore |
| 8,172,129 | B1 | 5/2012 | Laurenzi et al. |
| 8,613,702 | B2 | 12/2013 | Feer et al. |
| 8,875,867 | B2 | 11/2014 | Ronchi |
| 8,992,445 | B2 | 3/2015 | Blondheim |
| 9,636,280 | B1 * | 5/2017 | Althallab ............... A61J 9/008 |
| 2005/0283327 | A1 | 12/2005 | Bowman et al. |
| 2006/0278597 | A1 | 12/2006 | Daugherty et al. |
| 2007/0014100 | A1 | 1/2007 | Perez et al. |
| 2008/0167579 | A1 | 7/2008 | Ezra |
| 2011/0087078 | A1 * | 4/2011 | Zemel ................. A61B 5/4312 |
| | | | 600/300 |
| 2011/0251510 | A1 | 10/2011 | Zemel |
| 2011/0270164 | A1 | 11/2011 | Bane |
| 2012/0302924 | A1 * | 11/2012 | Cunningham ......... A61B 5/682 |
| | | | 600/590 |
| 2013/0073211 | A1 | 3/2013 | Hershkovich |
| 2013/0275171 | A1 | 10/2013 | Ulwick et al. |
| 2014/0013509 | A1 | 1/2014 | Gravett |
| 2014/0311239 | A1 * | 10/2014 | Marjanovic ............ G01G 21/28 |
| | | | 73/296 |
| 2015/0196247 | A1 | 7/2015 | Lau |
| 2016/0058361 | A1 * | 3/2016 | Melamed ............ G01N 33/487 |
| | | | 600/584 |

FOREIGN PATENT DOCUMENTS

| | | |
|---|---|---|
| EP | 1827210 | 9/2007 |
| WO | 2000009006 | 2/2000 |
| WO | 2009093238 | 7/2009 |
| WO | 2011144984 | 11/2011 |
| WO | 2012174315 | 12/2012 |
| WO | 2014064680 | 5/2014 |
| WO | 2014081401 | 5/2014 |
| WO | 2015040610 | 3/2015 |
| WO | 2015127514 | 9/2015 |
| WO | 2017045902 | 3/2017 |
| WO | 2017186504 | 11/2017 |

OTHER PUBLICATIONS

"Smart Bottles Sleevely" on-line at http://www.sleevely.com/blog/201451/sleevely-track-your-babys-nutrition 2014, 1page.

Zhu, Zhihua, et al. "Wearable sensor systems for infants." Sensors 15.2 (2015): 3721-3749.

Nyengele, Gedeon K. "A Mobile System to Monitor Neonatal Nursing Characteristics." SUNFEST (2013): 71.

Solasubbu, et al., "Multi-Parameter Monitoring System for Oral Feeding of Premature Infants Using Zig Bee". International Journal of Advanced Research in Biology Engineering Science and Technology (IJARBEST) vol. 2, Issue 3, Mar. 2016. Available: http://ijarbest.com/mm-admin/jornal/v2i3/document_2_iB Pu_31032016.pdf.

Taffoni, Fabrizio, et al. "Ecological sucking monitoring of newborns." IEEE Sensors Journal 13.11 (2013): 4561-4568.

Tamilia, Eleonora, et al. "Technological solutions and main indices for the assessment of newborns' nutritive sucking: a review." Sensors 14.1 (2014): 634-658.

Selley, W. G., et al. "Coordination of sucking, swallowing and breathing in the newborn: its relationship to infant feeding and normal development." International Journal of Language & Communication Disorders 25.3 (1990): 311-327.

Gewolb, Ira H., et al. "Developmental patterns of rhythmic suck and swallow in preterm infants." Developmental medicine and child neurology 43.1 (2001): 22-27.

* cited by examiner

FIG. 1A  PRIOR ART

FIG. 1B   Fully assembled Instrumented Bottle

Figure 2: Detachable bottom of the Instrumented Bottle, containing pressure sensor, release valve, and camera.

*Figure 3:* Pressure sensor signal captured by the Instrumented Bottle

*Figure 4:* Pressure sensor signal with detected sucks during infant meal

*Figure 5: Cumulative suck count across time*

*Figure 6: Bottle orientation*

*Figure 7: Sucking strength across meal as detected by pressure sensor on instrumented bottle*

*Figure 8: Sucking bursts during meal*

*Figure 9:* Images from bottle camera taken during meal

*Figure 10:* Oral feeding system with synchronized pressure support and mandatory volumes. When sucking pressure reaches a preset threshold, in this case – 40 mmHg (other thresholds may be used), the device delivers a predetermined amount of milk/formula (rate) during a feeding cycle.

INSTRUMENTED INFANT FEEDING BOTTLE

CROSS REFERENCE TO RELATED APPLICATIONS

This application claims priority to and incorporates by reference U.S. Provisional Patent Application Ser. No. 62/751,069 filed on Oct. 26, 2018 and entitled Instrumented Infant Feeding Bottle.

STATEMENT REGARDING FEDERALLY SPONSORED RESEARCH OR DEVELOPMENT

An application for NIH funding has been submitted for review. The Applicant will update this statement in due course.

BACKGROUND OF THE EMBODIMENTS OF THIS DISCLOSURE

Infancy is a critical window for physical and neurodevelopmental growth. There are lifelong implications for infants with patterns of growth that are too slow or too fast. In healthy term infants, those who gain weight too rapidly are more likely to become obese and have greater risk for comorbid metabolic health conditions, such as type 2 diabetes. On the other hand, slow growth is the hallmark for an underlying problem that needs to be addressed to assure survival. For preterm or medically fragile infants, sustained growth is imperative for survival, but over the long-term, these infants face similar life-long consequences as the healthy term infants if they gain weight too rapidly.

There are a number of factors that impact infant rate of growth and most are mediated through infant feeding. The ability to observe and measure factors related to feeding, and the objective assessment of meals, would permit intervention prior to growth being significantly impacted with consequent lifelong health implications.

Existing methods to assess infant feeding are limited. Total energy intake can be calculated from the dilution of stable isotopes across time; however, this method is cost prohibitive and provides no information about meal and sucking patterns. Frequency of meals and meal volume of bottle-fed infants can be assessed by caregiver diary or recall, but overestimation is common. Obtaining pre- and post-weights of the infant or bottle improves accuracy, but also increases the burden on caregivers and can be difficult with hungry and fussy infants. Some nutritive sucking behaviors such as suck count, burst duration, and pauses in sucking have previously been coded from videotapes of meals and/or with an apparatus containing a pressure transducer attached to the breast or bottle nipple, but neither procedure is practical for the assessment of multiple meals in large cohorts, or for studies conducted in the home environment. Infant behaviors around meals and caregiver practices are usually assessed via report from the caregivers themselves, which introduces considerable subjectivity, or via time-consuming coding of videotaped meal interactions.

Consequently, there are two overall objectives that need to be addressed:

(1) develop a method to identify infants with sucking and feeding patterns that place them at risk for rapid growth or growth failure; and (2) develop strategies to optimize feeding among infants who are at risk for excess growth or growth failure.

BRIEF SUMMARY OF THE DISCLOSURE

In a first embodiment claimed herein, a feeding bottle includes a bottle enclosure defining a hollow bottle chamber, wherein the enclosure defines a feeding outlet at a first end and an attachment structure at a second end. A bottom housing defines an instrument compartment extending between a closed exterior portion of the bottom housing and a separation surface within the bottom housing, wherein the bottom housing is configured for detachable connection to the attachment structure of the bottle enclosure. A relief valve is positioned within the separation surface of the bottom housing. A pressure sensor is positioned adjacent the separation surface of the bottom housing and connected by a passageway to the instrument compartment in the bottom housing, wherein the pressure sensor is configured to detect changes of pressure in the bottle enclosure.

In another embodiment, a feeding bottle defines a bottle enclosure that, in turn, defines a feeding outlet at a first end and an attachment structure at a second end. A bottom housing defines an instrument compartment extending between a closed exterior portion of the bottom housing and a separation surface within the bottom housing, wherein the bottom housing is configured for detachable connection to the attachment structure of the bottle enclosure. A computer within the instrument compartment has at least a processor and memory storing computer executable software therein. A relief valve is positioned within the separation surface of the bottom housing. A pressure sensor is positioned adjacent the separation surface of the bottom housing and connected by a passageway to the instrument compartment in the bottom housing; at least one actuator controlled by the computer and connected to the bottle enclosure controls a rate of fluid discharge at the feeding outlet according to the software. The pressure sensor is configured to detect changes of pressure in the bottle enclosure for synchronizing the rate of fluid discharge produced by the actuator.

In another embodiment, a computer implemented method of monitoring and controlling passaging of feeding substances from a bottle enclosure includes steps based upon measuring a series of sucking pressures with a pressure sensor in fluid communication with a hollow bottle chamber at least partially surrounded by the bottle enclosure; transmitting the sucking pressures from the pressure sensor to a computer; calculating a volume of the feeding substances exiting the hollow bottle chamber from sucking pressure data received at the computer; and controlling a triggering command that provides control data to an actuator that synchronizes a known volume of the feeding substances out of the hollow bottle chamber relative to the sucking pressure data.

The method may optionally include, for respective sucking events leading to passage of feeding substances from the hollow bottle chamber, measuring sucking pressures with a pressure sensor in fluid communication with a hollow bottle chamber at least partially surrounded by the bottle enclosure; transmitting the sucking pressures from the pressure sensor to a computer; using computerized software to calculate feeding pattern data from the sucking pressures over a period of time exhibiting a plurality of sucking events; and storing the feeding pattern data in memory associated with the computer.

A system according to this disclosure may incorporate a bottle enclosure defining a hollow bottle chamber, wherein the enclosure defines a feeding outlet at a first end and an attachment structure at a second end. A bottom housing defines an instrument compartment extending between a closed exterior portion of the bottom housing and a separation surface within the bottom housing, wherein the bottom housing is configured for detachable connection to the attachment structure of the bottle enclosure. A relief valve may be positioned within the separation surface of the bottom housing. A pressure sensor positioned adjacent the separation surface of the bottom housing and connected by a passageway to the instrument compartment in the bottom housing, wherein the pressure sensor is configured to detect changes of pressure in the bottle enclosure. A computer may be positioned within the instrument compartment and in data communication with the pressure sensor. At least one audiovisual accessory may also be positioned proximately to the bottle enclosure and configured to collect environmental sensor data related to the bottle enclosure, wherein the audiovisual accessory is in electronic communication with the computer.

DETAILED DESCRIPTION

The embodiments of this disclosure as described herein may be used for monitoring of infant feeding in full term and pre-term infants. The device can have multiple uses, including measurement of sucking pressures in infants at different gestational ages to determine normative data, objective measurements of readiness for oral feeding, and individualized oral feeding plans for infants at risk for oral dysfunction/aversion. The device, method and system of this disclosure may also be used for monitoring and advising about parental bottle-feeding practices.

In addition, some infants may have feeding problems that prevent them from developing sufficient sucking pressures, and efficient and fluent milk consumption. In this case, the sensing mechanism may be used in combination with an active assist mechanism that would deliver the milk or formula in sync with the infant's sucking. As such, the device will help with early and successful transition from tube feeding to oral feeding in infants with poor oral skills, particularly premature infants in which early establishment of oral feeding has been associated with superior motor skills in early childhood. The device may also be useful to provide individualized oral nutrition to infants with debilitating respiratory and gastrointestinal diseases in which oral feeding is usually contraindicated, or infants for whom there is an oral-motor or neurological reason that underlies their failure to thrive.

This disclosure includes numerous embodiments that utilize a bottle enclosure from which an individual (or even an animal in veterinary cases) can feed by sucking (e.g., through a nipple in one non-limiting embodiment.) The nutrition that passes from the bottle enclosure to the feeding individual or animal is not limited to any one kind of food, formula, or even any one thickness, liquid or solid state, or viscosity. Any substance that a user desires to move from the bottle enclosure to another entity or structure can make use of the feeding apparatus, system and method disclosed herein. Accordingly, terms such as "fluid," "nutritional substance," "meal," "fluid discharge" and the like have their broadest plain meaning without limitation. The terms describing contents of a bottle enclosure may include liquids, other materials of low viscosity, suspensions, water, milk, infant nutrition formulas, or any similar substance under consideration.

The embodiments of this disclosure address the following monitoring, assessment, and intervention needs:

Monitor meal frequency and meal size: Infants with atypical growth patterns often also have sub-optimal feeding patterns. Meals may be too frequent or infrequent, and may be too large or too small. The embodiments of this disclosure objectively assess meal timing, frequency, size, and duration, without the need for caregivers to self-report (which introduces bias and error through forgetfulness etc.) or to turn on/off switches to record meals.

Assess sucking behaviors during meals: Growth depends on an infants' ability to suck for nutritive purposes. Infants with vigorous sucking are at risk for rapid growth and future obesity, whereas those with poor sucking vigor, dysfluent sucking, or uncoordinated suck-swallow-respiration, such as preterm and medically fragile infants, are at risk for growth failure. The intervention apparatus, method, and system disclosed herein objectively characterize and quantify suck counts, sucking rate and frequency, sucking strength, volume of consumption per suck, and changes in these metrics across the meal and between meals, along with pauses in sucking.

Assess caregiver feeding practices: Caregiver actions play an integral role in infant feeding. They need to recognize infant hunger and fullness cues, infant readiness to accept a bottle, and infant reluctance to feed. For infants who are preterm or medically fragile, caregivers may need to orient the bottle at a specific angle to facilitate optimal feeding. For example, some infants require "paced" feeds whereby the bottle is oriented horizontally so that the nipple is not completely filled with milk and thereby, infants avoid the risk of taking too much fluid into their mouths with one suck. In addition, caregivers use different strategies to encourage infants to finish feeds, which is a known risk factor for future obesity, such as tilting the bottle up to an almost vertical position, or rotating or shaking the bottle when the infant's sucking slows down. The embodiments of this disclosure contain an accelerometer to monitor bottle orientation and movement. A gentle alarm can also be fitted to the bottle to alert caregivers when the bottle orientation is not optimal. The alarm can be a vibration, a light, a sound, or other cues that draw attention to a specified condition.

Assess infant cues and behavior or temperament around meals, and conditions under which meals begin and end: Under optimal feeding conditions, infants display signs of hunger when ready to eat (such as sucking on a fist, making sucking sounds, or giving a distinctive "hunger" cry), and signs of fullness when they are finished (e.g. turning head away from the bottle, sleeping, chewing rather than sucking on the nipple). Parents should respond to these cues, but some infants do not display clear and consistent hunger and fullness cues. Further, some infants have a difficult or fussy temperament, which could lead to parental overfeeding when they use food to soothe the infant. The embodiments of this disclosure contain a mounting for a camera and microphone, and image/audio processing techniques will be used to characterize infant readiness to feed, fullness cues, infant temperament, status (awake-calm, awake-fussy, asleep) and crying prior to, during, and after meals, as well as whether milk remains in the bottle when the meal ends.

Assess energy content of the liquid consumed: Methods to objectively and accurately assess energy intake are difficult and expensive. Studies of infants usually rely on parent report but this method is fraught with bias and burden. The embodiments of this disclosure will use multispectral analysis to derive the energy density of the milk or formula used for feeding, and this combined with the meal size, can be used to determine energy intake.

Method to provide summary reports to caregivers and providers: When feeding or growth problems occur, providers typically rely on caregiver reports to try to identify problematic feeding behaviors or caregiver practices. Data collected with this intervention will be used to define the range of infant sucking and meal patterns that supports optimal growth, and summary reports can then be generated to inform providers and caregivers about how the infant's behavior compares to typical patterns. Similarly, reports that summarize caregiver practices can be generated and provide feedback during interventions.

Method to assess readiness to feed in premature or medically compromised infants, and feeding difficulties in infants with failure to thrive: Infants who are premature or medically compromised are often fed with orogastric tubes. Readiness to begin oral feeds is based on the subjective assessment of the providers, through observation of the infant's cues. Some of these infants may not yet be capable of coordinating suck-swallow-breathing, and may even be averse to oral feeds following dependence on orogastric feeding tubes. The same is true for medically compromised infants. Infants with failure to thrive may also exhibit weak and ineffective sucking, aversions to oral feeds, and low consumption volume. The embodiments of this disclosure will assess readiness to feed in premature or medically compromised infants, and problematic sucking and meal patterns of those with failure to thrive through methods including but not limited to: sucking strength and stamina, sucking consistency, efficiency of intake, and changes across meals. Data from the embodiments of this disclosure can also be integrated with data from medical monitors (e.g. respiration, heart rate, etc.) to identify physiological correlates of pauses in sucking or other inconsistent sucking patterns.

Intervention with an assistive device: Infants who are premature or medically compromised may require intervention to facilitate controlled delivery of milk to the infant. The embodiments of this disclosure can be fitted with a regulatory vacuum that delivers a specific volume of milk per suck, based in part upon real time feedback from the monitoring sensors.

Example Sensors

Figure 1A:
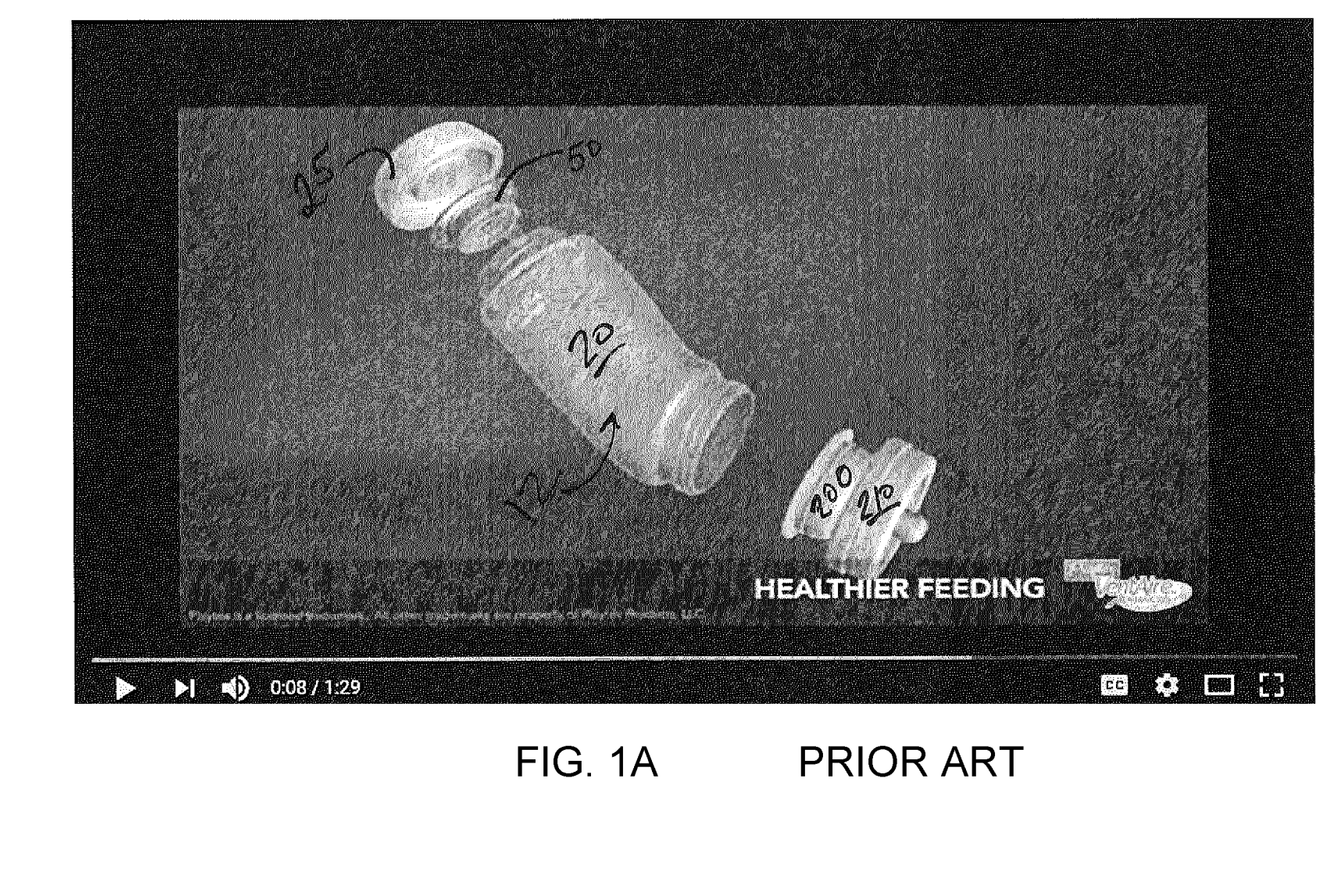
FIG. 1A is a PRIOR ART view of a traditional feeding bottle.
Figure 1B:
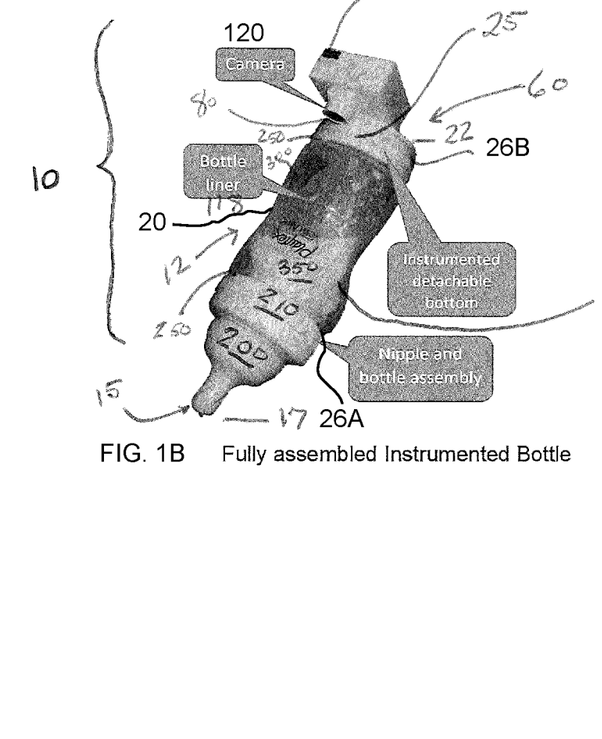
FIG. 1B is a perspective view of a fully assembled instrumented bottle according to this disclosure.
Figure 2:
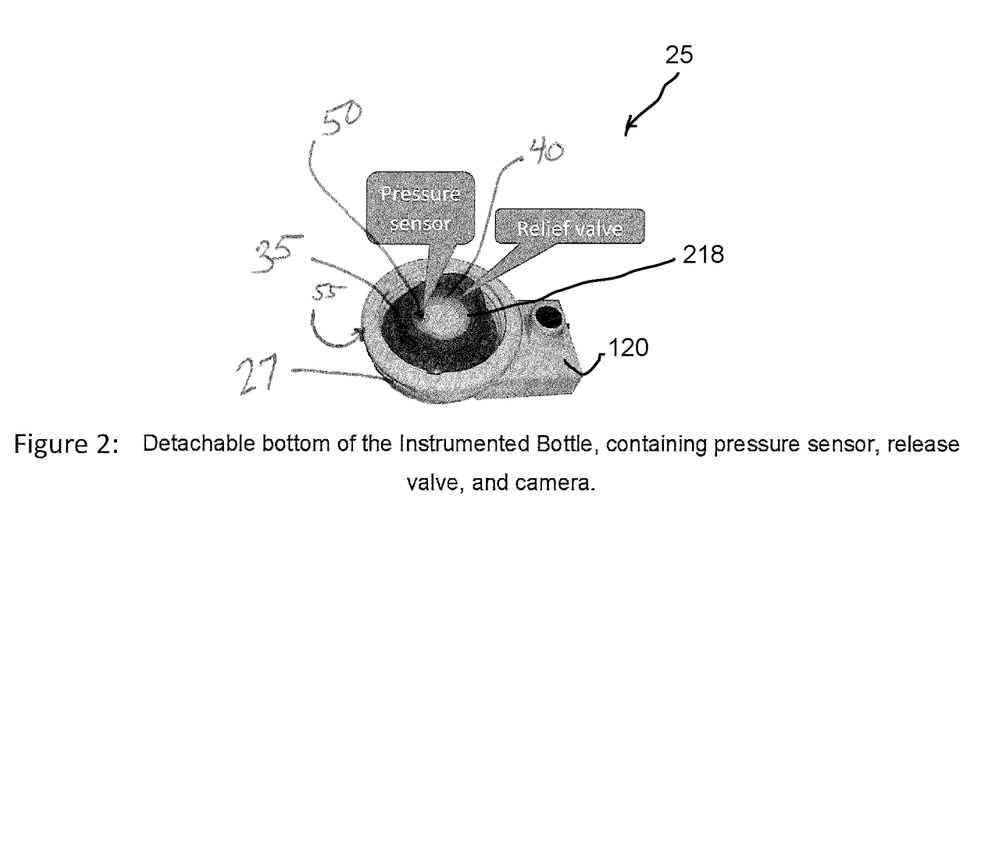
FIG. 2 is a top perspective view of a detachable bottom of the instrumented bottle, containing pressure sensor, release valve, and camera as described herein.
Figure 3:
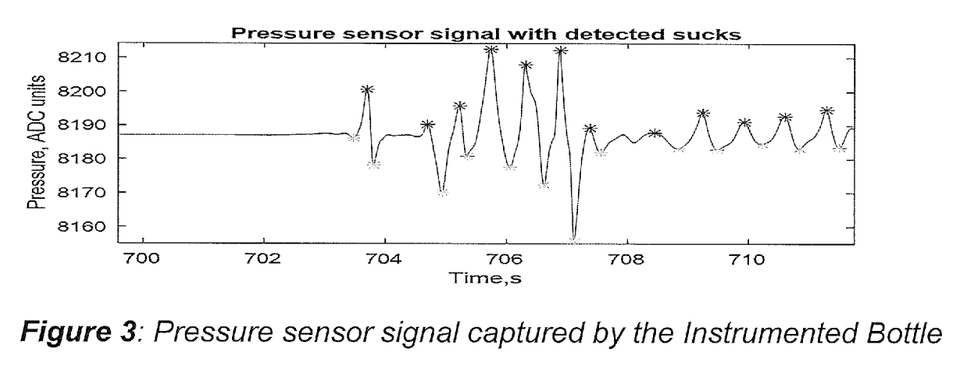
FIG. 3 is a schematic plot of an output pressure sensor signal captured by the instrumented bottle disclosed herein.
Figure 4:
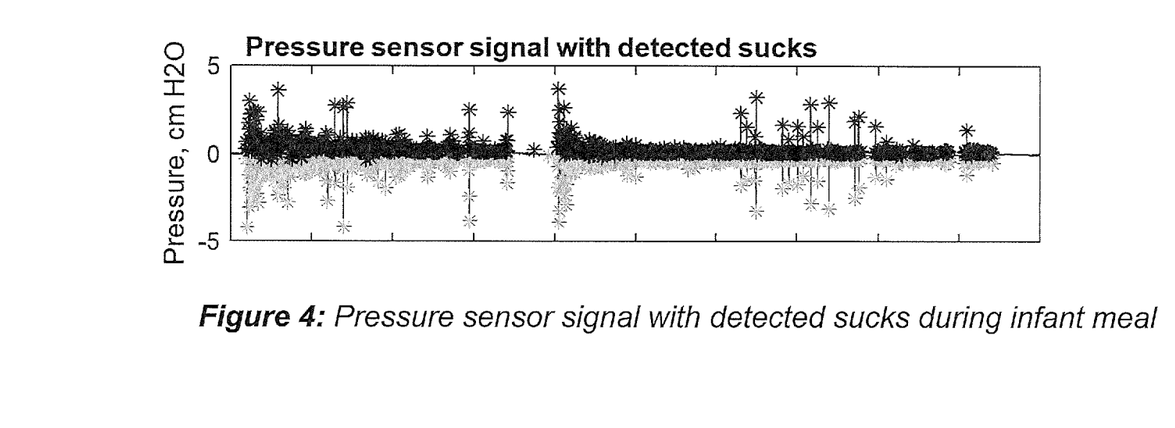
FIG. 4 is a schematic plot of an output pressure sensor signal with detected sucks during an infant meal as disclosed herein.
Figure 5:
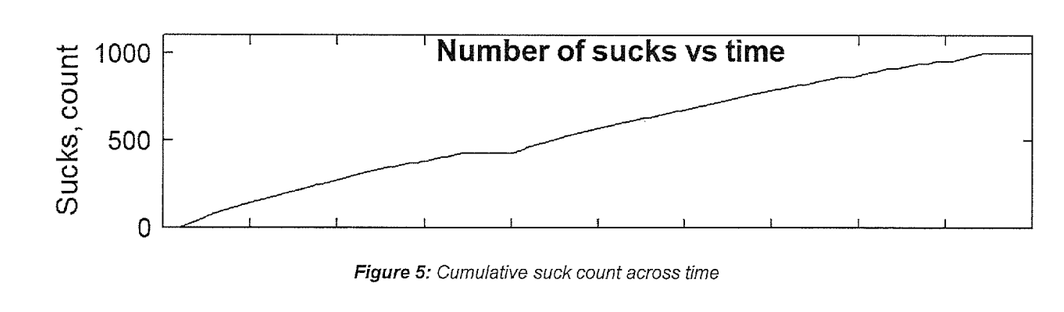
FIG. 5 is a schematic plot of cumulative suck count across time.

One non-limiting design of the instrumented bottle (the "IB") is shown in FIG. 1B. Without limiting this disclosure to any one embodiment, a non-limiting example test structure of the IB of FIG. 1B is based on the commercially available Playtex VentAire® bottle shown in exploded format in FIG. 1A, but any infant bottle could be modified to accommodate the instrumentation. The bottle cap 210, the nipple 200, a bottle enclosure 20, and a bottle chamber 12 of a feeding bottle structure 10 are not necessarily modified to fulfill the goals of this disclosure. The electronics and sensors described below are placed in a detachable bottom housing 25, that in the original bottle contains a pressure relief valve 50. In creating one non-limiting test prototype, a 3 mm opening is drilled into the bottom of the detachable bottom housing 25. A rigid tube or other conduit for fluid or gas flow connects the inside cavity, or bottle chamber 12, defined within the bottle enclosure 20, with a digital 14-bit pressure sensor 50, that may be, without limitation, a MEMS pressure sensor (e.g., model number SM9541, range ±10 cm $H2O$, Silicon Microstructures, Inc.™) housed on a printed circuit board inside the detachable bottom housing 25. The contents of the bottle enclosure 20 are separated from the pressure sensor 50 by a disposable liner 118 (e.g., Playtex Drop-Ins®) which is a thin and flexible closed pouch for the milk or feeding substance 350. The use of a liner 118 simplifies sterilization of the instrumented bottle structure 10 between uses, as the pressure sensor 50 never comes in direct contact with the milk or other feeding substance 350. The bottle enclosure 20, bottle chamber 12, cap 210, and nipple 200 can be sterilized traditionally by boiling or placed in a dishwasher, while the detachable bottom housing 25 can be sterilized chemically or by UV light. Each suck from an infant changes the pressure in the liner, or membrane, 118 collapses the liner and generates negative pressure in the inside chamber 12 of the bottle enclosure 20 that is registered by the pressure sensor 50. The reduced pressure causes the relief valve 40 to open and restore the pressure inside the instrumented bottle structure 10, back to the atmospheric pressure, creating a distinct signal on the output of the pressure sensor 50 (FIG. 2). An additional flexible membrane may be used on top of the pressure sensor 50 to make the design liquid-proof and further simplify sterilization. One feature of the proposed design is separation of the liquid 350 being consumed (milk or formula) from the pressure sensor. Unlike designs discussed in prior art, this bottle does not contain catheters that need to be primed prior to use and are difficult to sterilize.

In one non-limiting example, the electronics of the instrumented bottle structure 10 are based on a microcontroller from STM32 family that samples the pressure sensor data at 128 Hz. A 3D accelerometer 70 (ADXL362 is used to measure the orientation of the bottle in respect to gravity). The accelerometer signal is sampled at 128 Hz. In addition, an OV5642/40 camera 120 is interfaced to the microcontroller using a frame buffer that converts parallel MIPI interface of the camera to a serial SPI interface. Any suitable microcontroller, pressure sensor, accelerometer and camera may be used in place of those listed. The camera is optional and may not be present. Alternate cameras can be fitted to enable continuous video recording, infrared recording, or any other imaging technology. The camera is configured to take an image of the infant's face at fixed intervals (for example, 0.1 s, 5 s, etc). Such images can be used to assess readiness and satiety cues, such as if the infant's mouth was open as the bottle approached (as a sign of readiness), whether the infant was crying prior to, during, or following meals, whether the nipple was still accessible to the infant during pauses in sucking, and the conditions under which the meal ends. The sensor signals and the images are stored on a 32 GB microSD card interfaced to the same microcontroller or transmitted wirelessly via Bluetooth or other suitable mechanism to deliver real-time data to smartphone or Internet.

Additional sensor may include a visible light/infrared emitter (such an LED or LED array) and a color sensor/camera embedded into the detachable base and looking at the milk/formula. Using principles of multi-spectral imaging, these sensors can differentiate in the nutrient and energy content of the liquid. Specifically, the fat content of milk or concentration of the formula may be measured by observing the difference in reflectance at different wavelengths. To measure the reflectance, the LED would illuminate the liquid inside of the liner at a certain light wavelength, for example, 800 nm, 900 nm, etc. The camera or color sensor would measure the intensity of light reflected by the liquid relative to the background reflectance. The measurements taken at several wavelength are used to establish the fat content of the liquid through regression analysis.

Actuators

The assistive part of the device may include various actuators that deliver a predefined volume of liquid into the infant's mouth. Such actuators may include, but not limited to, piezoelectric or electromechanical devices that may also be mounted within the instrumented bottle structure 10, proximate the bottle's bottom housing 25. The actuator may momentarily increase the air pressure between the liner 118 and the bottle enclosure 20 to stimulate milk/formula 350 delivery at lower sucking pressures. Alternatively, a syringe or a pump-like device may be used with a flexible catheter to inject a predefined volume directly into the oral cavity, bypassing the nipple.

Processing and Extraction of Useful Information

The current prototype is not limiting of this disclosure and can also be used to train parents to improve their feeding practices (e.g. learning their infants' hunger and fullness cues, etc.) With modifications, the instrumented bottle structure 10 can also be used not only as an assessment tool but also as an assistive device that will be able to synchronize the mechanical sucking pressure generated by the infant with the delivery of a pre-specified feeding volume. This assistance operation may be the result of a real time interaction between the pressure sensor (input) and the triggering system (output). As an assistive device, the device can have multiple uses, including measurement of sucking pressures in infants at different gestational ages to determine normative data, objective measurements of readiness for oral feeding, and individualized oral feeding plans for infants at risk for oral dysfunction/aversion. By addressing these needs, our embodiments of this disclosure will facilitate healthy infant feeding and thereby optimize and regulate infant growth.

The processing of the pressure sensor signal may be performed in several steps. First, the signal from the pressure sensor 50 was converted into the centimeters of water using the manufacturer-provided equations. Such conversion is useful, but not mandatory for suck counting. Second, the signal is de-noised using wavelet denoising technique. The threshold for elimination of small wavelet coefficients may be established empirically as the minimal value that eliminates pressure signal variations in an undisturbed bottle. Simpler techniques, such as running average smoother may also be used or the signal could be used unfiltered.

Suck count estimation is performed by a non-derivative based peak detection algorithm. The minimal signal change required to detect signal minima (peaks) or maxima (valleys) is set to be twice the noise threshold used in the wavelet denoising. The suck count is estimated as: sucks=(peaks+valleys)/2. Cumulative suck count is computed as the running total from the start of experiment. Alternatively, suck count may be estimated as the number of mean crossings of the sensor signal.

Meal initiation/termination detection. An initiation of a new meal is counted when the bottle detects sucking after a period of inactivity. Correspondingly, the meal is considered terminated after no sucking is detected for a period of time. The bottle position and camera images may be utilized as secondary predictors if needed.

Figure 6:
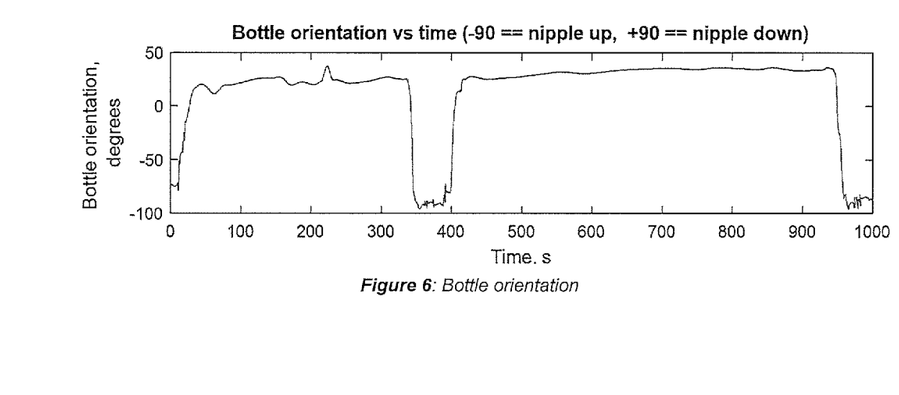
FIG. 6 is a schematic plot of bottle orientation as sensed by instrumentation disclosed herein.

Measurement of bottle orientation. Bottle orientation is a good indication whether the bottle is in position conducive to milk flow and can be used as a secondary predictor in other algorithms (such as detecting pauses in feeding). The accelerometer signal is used to compute the tilt angle of the bottle in respect to gravity using standard formulas. FIG. 6 shows the pitch angle of the bottle.

Detection of intra-meal pauses. As shown in FIG. 6, the intra-meal pauses (e.g. for burping/diaper change) manifest as interruptions in sucking and as a change in the bottle position (nipple up to avoid spilling). Pause detection may be performed using two approaches: 1) no sucking for a period of time and nipple up position of the bottle; 2) no sucking for a short period of time, less than that for meal termination detection.

Figure 7:
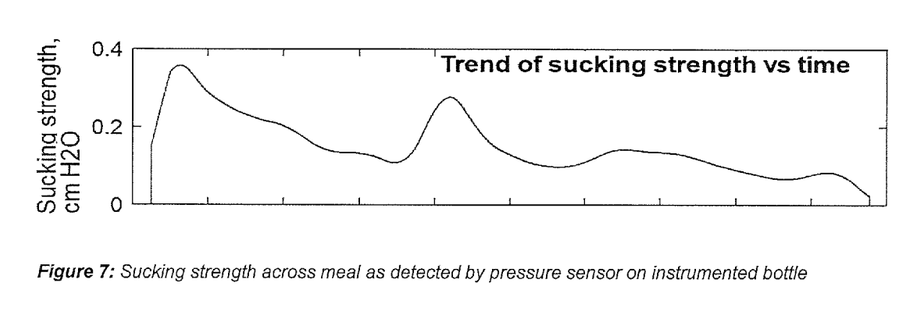
FIG. 7 is a schematic plot of sucking strength across meal as detected by pressure sensor on an instrumented bottle according to this disclosure.

Measurement of sucking strength. The strength of a suck is proportional to the amount of pressure change measured by the pressure sensor. The sucking strength may be expressed in pressure units (e.g. PSI) or normalized and smoothed by a kernel function (FIG. 7) to express the trend over time. The accuracy of sucking strength measurement may be established by applying a predefined volume change created at the nipple by using a syringe. The change of pressure inside of the bottle is proportional to the change in volume: $\Delta P = P/V \Delta V$, where $P\_0$ is atmospheric pressure and V is volume inside of the bottle. Therefore, a known change in volume should produce a known change in pressure that will be compared to the actual sensor reading and used in computation of accuracy.

Measurement of sucking volume (ml) and volumetric rate of consumption (ml/s). Using the principles discussed for measurement of sucking strength, the volume consumed in an individual suck is $$\Delta V = \frac{V}{P} \Delta P.$$

Given the known atmospheric pressure $P_0$ and known capacity of the bottle liner $V_0$, the total volume consumed by an infant can be estimated as:

$$V_T = \alpha \sum_{i=1}^{N} \Delta V_i, \Delta V_i = \frac{V_i}{P_0} \Delta P, V_i = V_0 - \sum_{1}^{i-1} \Delta V_i,$$

where N is the number of sucks, $\Delta V_i$ is the volume of i-th suck, $V_i$ is the remaining liquid volume after i sucks, and a is the spillage coefficient that will be determined from the study data. The volumetric rate of consumption as a function of time V(t) ml/s and average rate of consumption $V_{AVF}$ (ml/s) may be estimated from individual sucks $\Delta V_i$. Alternatively, numerical analysis of fluid dynamics may be performed to develop equations connecting the pressure measurement with the liquid consumption. Camera-based techniques could also be used as described in camera image processing.

Figure 8:
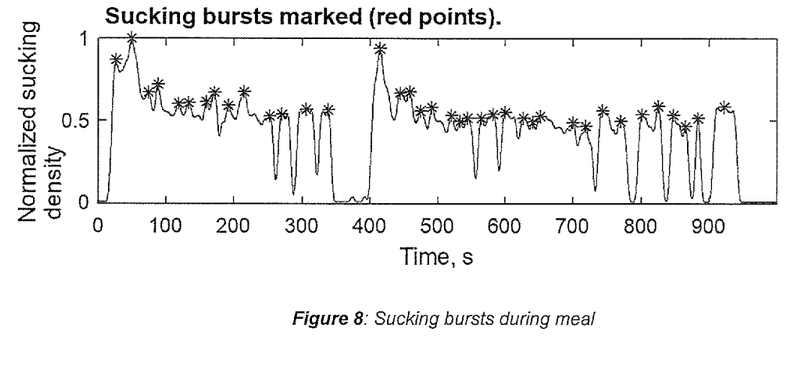
FIG. 8 is a schematic plot of sucking bursts during meal activity as disclosed herein.

Measurement of count, duration of sucking bursts and breaks between bursts. As shown in FIG. 8, the temporal density of sucks computed by a Gaussian kernel function provides an excellent estimate of sucking bursts. Specifically, the method uses a sliding Gaussian window of a fixed width. If the window covers just a few sucks, the temporal density of sucking is low. If a window covers more sucks, the temporal density of sucks is high. The valleys of the temporal density correspond to the short breaks between sucking bursts and peaks correspond to sucking bursts. Both peaks and valleys can be easily detected by the peak detection algorithm. The duration of the burst (s) and duration of the break between bursts (s) may be computed by applying an adaptive threshold scaled by the peak density. The parameters of the algorithm (e.g. window width) may be estimated from experimental data.

The following metrics may be extracted using image analysis. Methods of deep learning, specifically, Convolutional Neural Networks (CNN) may be to recognize the contextual information in the image.

Estimation of infant's facial expression (e.g. infant cry vs. calm prior to meal). The image analysis may identify the facial expression of the infant. The camera starts capturing images when the accelerometer indicates motion (handling of the bottle) and therefore will capture infant's face prior to meal initiation. Using standard face recognition techniques, the face of the infant may be separated from the image background. The face image is scaled and associated with a facial expression label assigned from the human annotation of the experiment. The following face expression labels may be used: "calm and awake", "crying", "eyes closed", "turning away", etc. Face/label pairs may be used to train a Support Vector Machine classifier operating on features extracted by a pre-trained CNN. Similar approach may be used to assess infant's readiness to feed (i.e. mouth open and oriented toward bottle as the bottle approaches).

Detection of caregiver holding infant during meal. Due to the camera's position and wide angle of view, a caregiver is always visible when the infant is being held. The image with infant's face removed may be processed by a similar algorithm to detect caregiver in the image. Specifically, each image is labeled by a human annotator as "caregiver present" (e.g. a hand, torso or clothing of a person holding the baby is visible) or "caregiver absent" (e.g. only the infant and background are visible). The images will be used to train an SVM classifier using features extracted by a pre-trained CNN.

Figure 9:
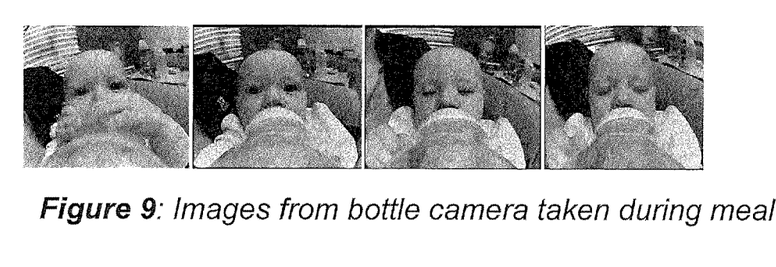
FIG. 9 is a series of time domain images from a bottle camera taken during meal as disclosed herein.
Figure 10:
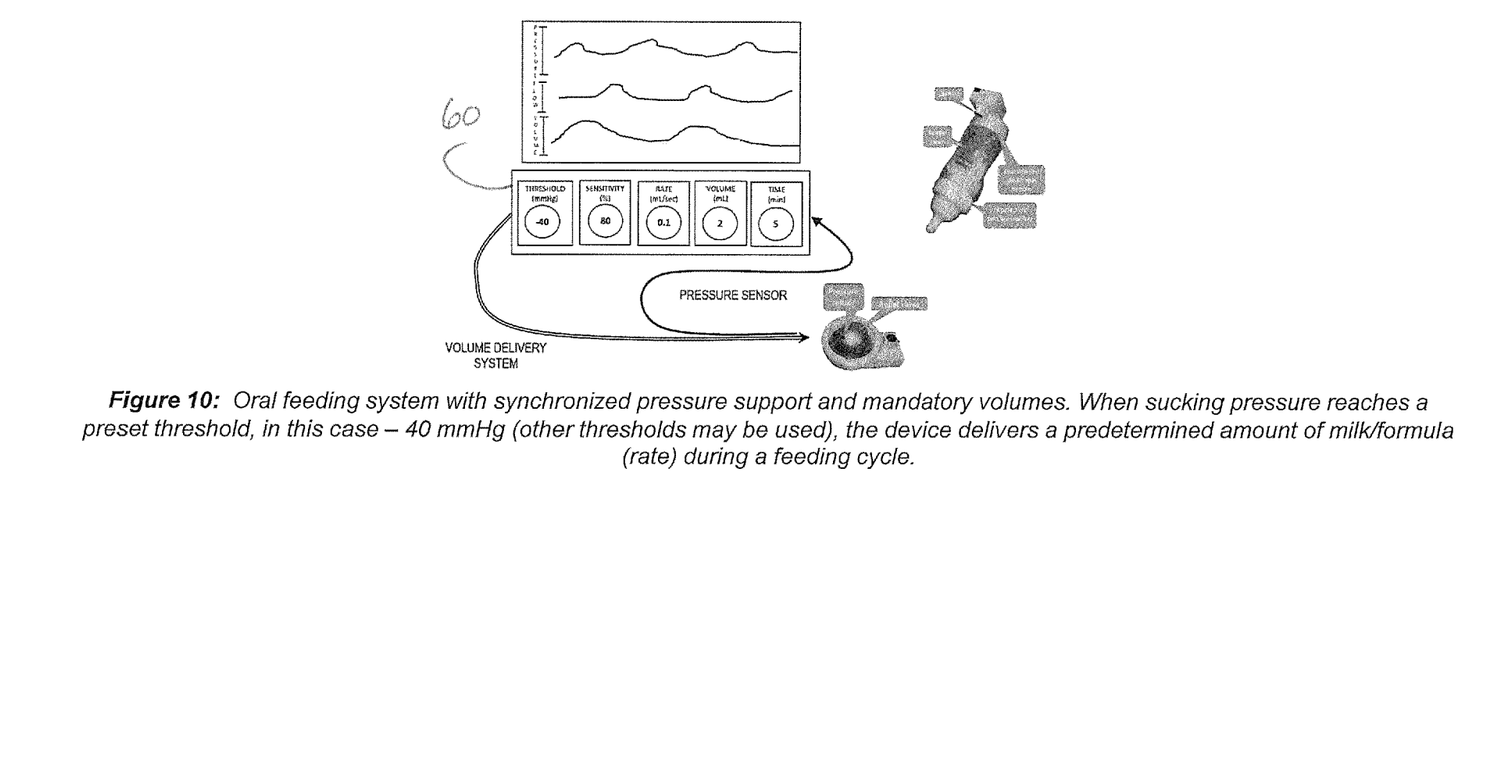
FIG. 10 is an oral feeding system with synchronized pressure support and mandatory volumes as disclosed herein.

Estimation of bottle emptying during a meal from images. The camera position ensures that the bottle content is always visible (FIG. 9, compare leftmost and rightmost images). Using known position of the milk container in the image (camera is fixed to the bottle, so the milk/formula will always be in the same place on the image) and color segmentation techniques to select the contiguous region of "off-white," the bottle emptying can be evaluated as the computed area of the milk/formula in the image to assess the consumed volume.

Detection of the conditions under which the meal ends (infant asleep, bottle empty, infant refusal, parent removing bottle). A similar image recognition approach may be used to determine why the meal ended. Termination time is known from the pressure sensor data and camera images around the termination time will be analyzed for infant's expression (e.g. eyes open/closed).

Assistance with feeding is performed by the actuator that delivers a metered volume of milk in a dose response to the sucking pressure the infant applies to the nipple. The ability to synchronize the mechanical sucking pressure generated by the infant with the delivery of a pre-specified feeding volume results from a real-time interaction between the pressure sensor (input) and the triggering system (output). Triggering of pre-specified feeding volumes occurs when the sucking pressure exceeds a set threshold.

Sucking strength measured by the pressure sensor in the IB that exceeds a certain threshold value indicates individual readiness for independent feeding. When the sucking strength exceeds the set threshold, the triggering system delivers of a pre-specified feeding volume. The operator sets ideal threshold, feeding volume, and gain or proportional assist option (sensitivity) to overcome mechanical impediments for delivery of an adequate positive pressure to deliver the pre-specified feeding volume. Alternatively, the device can be programmed to deliver specific volumes after specific sucking patterns and/or number of sucks (e.g. 0.1 mL volume delivered after every 2-3 recorded nutritive sucks) over a specific period of time. The system will be able to record the sucking strength and volume of fluid delivered per suck during a feeding session.

The estimated mass of a premature infant is 500-2,500 grams (depending on gestational age), and the initial feeding volume is anticipated to be 2 mL. Feeding volumes are increased 10-20 mL/kg/day. Based on these volumes, it is anticipated the volumetric delivery of fluid will need to have an accuracy of ±0.1 mL and a resolution of 0.1 mL per suck. Alternatively, the bottle may be programmed to deliver a volume after recording a defined number of sucks (e.g. 0.1 mL volume delivered after every 2-3 recorded nutritive sucks). The average feeding volume of a premature infant is 30 mL. Sucking pressures will be monitored by a pressure sensor which is equipped with a gain (sensitivity) control. Recorded sucking pressures must exceed a certain threshold value (~40 mmHg) before a volume of fluid is delivered, and the sensitivity controller specifies the rate at which increased volume is delivered for increasing levels of sucking pressures.

Example 1

The instrumented bottle 10 objectively measures sucking count and pressure, and then these variables can be used to derive an estimate of meal volume. Testing at the bench confirms that the decrease in pressure detected by the pressure sensor within the bottle is proportional to the volume of a given suck, thus providing a method to quantitate individual sucks, and to measure the ingested volume and strength of sucking. Testing has also established that the data from the accelerometer 70 reliably detects orientation of the bottle structure 10, and can be combined with the image data to determine whether the bottle is accessible to the infant when it is oriented in a feeding position, and whether the infant's mouth is open as the bottle approaches, which indicates readiness to receive the bottle. Images from the camera are also useful to characterize infant temperament immediately prior to feeding (e.g. crying vs. calm), readiness to accept the bottle (i.e. mouth open as the bottle approaches), infant disposition at the end of the meal (e.g. eyes closed/sleeping vs. calm/alert vs. turning away and distress), and whether any milk remains in the bottle at the end of the meal.

Example In-vitro Data Collection

The nipple of the instrumented bottle 10 filled with 60 ml of infant formula (Similac Sensitive™; Abbott Nutrition), was attached to a commercial breast pump (Medela Freestyle; Medela LLC), capable of varying the strength and frequency of sucking. The data from IB were collected using 6 combinations of preset frequencies ("slow"—0.98 Hz and "fast"—1.44 Hz) and strengths (levels 2-minimum, 4-medium, and 6-maximum as defined the manufacturer of the breast pump). Each data collection contained a single bout of sucking approximately 90 seconds in duration.

The simulated meal was videotaped.

TABLE 1

The results of in-vitro testing.

| Strength | Frequency | Number of sucks, video annotation | Number of sucks, IB | Error, % |
|---|---|---|---|---|
| 2 | Slow | 113 | 114 | 0.88% |
| 2 | Fast | 166 | 168 | 1.19% |
| 4 | Slow | 98 | 103 | 4.85% |
| 4 | Fast | 167 | 170 | 1.76% |
| 6 | Slow | 88 | 90 | 2.22% |
| 6 | Fast | 167 | 169 | 1.18% |
| | | | Mean error | 2.02% |
| | | | Standard deviation | 1.47% |

In a first embodiment claimed herein, an instrumented feeding bottle 10 includes a bottle enclosure 20 defining a hollow bottle chamber 12, wherein the bottle enclosure 20 defines a feeding outlet 15 at a first end 17 and an attachment structure 26 at a second end 22. In one non-limiting embodiment, the attachment structure 26 may be threading 250, but this disclosure encompasses other manners and mechanisms of attaching a cap 210 and bottom housing 25 to a bottle enclosure 20. A bottom housing 25 defines an instrument compartment 27 extending between a closed exterior portion of the bottom housing and a separation surface 35 within the bottom housing, wherein the bottom housing is configured for detachable connection to the attachment structure 26 of the bottle enclosure. A relief valve 40 is positioned within the separation surface of the bottom housing. A pressure sensor 50 is positioned adjacent the separation surface of the bottom housing and connected by a tube, conduit or other passageway 55 to the instrument compartment 27 in the bottom housing 25, wherein the pressure sensor 50 is configured to detect changes of pressure in the bottle enclosure 20.

The instrumented feeding bottle 10 includes, in at least one embodiment, a computer 60 having at least a power source, a processor and memory storing computer implemented software, wherein the computer is configured to receive pressure data from the pressure sensor. The software is configured with computer readable commands that utilize the pressure data and changes in the pressure data to track feeding patterns from the feeding outlet 15. The feeding patterns calculated by the computer 60 comprise at least one of the following: measurements of suck counts, sucking rate and frequency, sucking strength, volume of consumption per suck, and changes in these metrics across a meal and between meals. The computer is configured to provide reports to assess volume consumed per meal, rate of consumption and changes in rate of consumption across the meal, sucking pauses and meal interruptions, meal frequency, meal timing, meal duration, and bottle orientation during the meal. An instrumented feeding bottle 10 according to this disclosure further has one non-limiting configuration with an accelerometer 70 in electronic communication with the computer to monitor bottle movement and orientation. The computer 60 may use an alarming function controlled by the computer to alert a caregiver to certain trigger conditions such as improper feeding bottle orientation. Similarly, an accessory such as a camera 120 may be connected to the computer.

A feeding bottle according to this disclosure may utilized a light source 80 configured to direct light from the bottom housing 25 into the hollow bottle chamber 12 and at least one light sensitive sensor 100 connected to the computer within the instrument compartment such that contents of the bottle enclosure can be analyzed for composition by image analysis. An instrumented feeding bottle 10 may use the light sensitive sensor to measure spectral compositions of light directed to contents of the hollow bottle chamber.

In one use example, the instrumented feeding bottle 10 may contain a nutritional substance within the hollow bottle chamber, wherein the nutritional substance is sufficiently fluidic to move from the hollow bottle chamber 12 through the feeding outlet 15, creating a change in pressure within the bottle enclosure 20 that is detectable by the pressure sensor 50. The feeding bottle 10 may be of a modular construction so that the bottle enclosure 20, a cap 210, a nipple 200, and an optional liner 118 configured for holding a nutritional substance within the hollow bottle chamber are all separable. In one embodiment, the liner separates the nutritional substance from the bottle enclosure 50 and the pressure sensor 20. An instrumented feeding bottle 10 may also include at least one membrane 218 separating a portion of the bottle enclosure 20 from the pressure sensor, wherein the portion of the bottle enclosure is configured to hold a nutritional substance between the bottle enclosure and the feeding outlet. The feeding outlet 15 at the first end 17 of the bottle enclosure 20 is a feeding nipple 200 configured to connect to a bottle cap 210 that detachably secures the feeding nipple 200 to the bottle enclosure 20. An instrumented feeding bottle 10 as described above has a bottle enclosure that defines a second attachment structure 26 for the bottle cap 210, and wherein the attachment structure 26A at the first end and the second attachment structure 26B at a second end of the bottle enclosure 20 comprise threading 250. In some embodiments, a passageway 55 between the pressure sensor 50 and the instrument compartment 27 is in the form of a tube or hollow region that provides a reference pressure from the instrument compartment 27 to the pressure sensor 50. Typically, the reference pressure is atmospheric pressure within the instrument compartment 27, and wherein a change in pressure within the bottle enclosure 20 is determined by comparison to the atmospheric pressure.

In another embodiment, a feeding bottle 10 defines a bottle enclosure 20 that, in turn, defines a feeding outlet 15 at a first end 7 and a respective attachment structure 26A, 26B at the first end 17 and a second end 22. A bottom housing 25 defines an instrument compartment 27 extending between a closed exterior portion of the bottom housing 25 and a separation surface 35 within the bottom housing, wherein the bottom housing is configured for detachable connection to the attachment structure 26B at the second end 22 of the bottle enclosure 20. A computer 60 within the instrument compartment 27 has at least a processor and memory storing computer executable software therein. A relief valve 40 is positioned within the separation surface 35 of the bottom housing. A pressure sensor 50 is positioned adjacent the separation surface 35 of the bottom housing 25 and connected by a passageway 35 to the instrument compartment in the bottom housing 25; at least one actuator controlled by the computer and connected to the bottle enclosure controls a rate of fluid discharge at the feeding outlet according to the software. The actuator may be any mechanical device that is controlled by the computer 60 to push the feeding substance 350 from the pouch of the liner 118. The actuator can be a clamping device, a plunger, corresponding plates on opposite sides of the liner, or other mechanical embodiments set up to squeeze or exert force on the liner to push the feeding substance out of the outlet 15.

The pressure sensor 50 is configured to detect changes of pressure in the bottle enclosure for synchronizing the rate of fluid discharge produced by the actuator. In this embodiment, a feeding bottle utilizes the actuator 300 as controlled by the software to expel a calculated volume of fluid discharge from the feeding outlet. A regulatory vacuum device connected to the computer may serve as the actuator in one non-limiting example to deliver a specific volume of nutritional fluid from the hollow bottle chamber in accordance with the changes of pressure in the bottle enclosure.

In another embodiment, a computer implemented method of monitoring and controlling passaging of feeding substances 350 from a bottle enclosure includes steps based upon measuring a series of sucking pressures with a pressure sensor in fluid communication with a hollow bottle chamber at least partially surrounded by the bottle enclosure; transmitting the sucking pressures from the pressure sensor to a computer; calculating a volume of the feeding substances exiting the hollow bottle chamber from sucking pressure data received at the computer; and controlling a triggering command that provides control data to an actuator that synchronizes a known volume of the feeding substances out of the hollow bottle chamber relative to the sucking pressure data.

This computer implemented method may include additional steps as follows, in no particular order:

measuring the number of suck events correlated with the sucking pressure data.

measuring movement and orientation of the bottle enclosure with an accelerometer in communication with the computer.

measuring sucking volume and volumetric rate of fluid exiting the bottle enclosure due to the sucking pressures.

calculating a temporal density of suck events with a Gaussian kernel function exhibiting a sliding Gaussian window allowing for detection of sucking bursts and breaks between bursts.

transmitting image data of an environment of use of the bottle enclosure from a camera encompassing a view of the bottle enclosure and/or a view of an individual feeding from the bottle.

The method may optionally include, for respective sucking events leading to passage of feeding substances from the hollow bottle chamber, measuring sucking pressures with a pressure sensor in fluid communication with a hollow bottle chamber at least partially surrounded by the bottle enclosure; transmitting the sucking pressures from the pressure sensor to a computer; using computerized software to calculate feeding pattern data from the sucking pressures over a period of time exhibiting a plurality of sucking events; and storing the feeding pattern data in memory associated with the computer.

Nonlimiting options for the method include calculating feeding pattern data from a frequency analysis of sucking events during the period of time, measuring sucking volume and volumetric rate of fluid exiting the bottle enclosure due to the sucking pressures, and correlating a series of sucking events to a single meal feeding period and further calculating total feeding volume of fluid ingested.

A system according to this disclosure may incorporate a bottle enclosure 20 defining a hollow bottle chamber 12, wherein the enclosure defines a feeding outlet 15 at a first end 17 and an attachment structure 26 at a second end. A bottom housing 25 defines an instrument compartment 27 extending between a closed exterior portion of the bottom housing 25 and a separation surface within the bottom housing 25, wherein the bottom housing 25 is configured for detachable connection to the attachment structure 26 of the bottle enclosure. A relief valve 40 may be positioned within the separation surface 35 of the bottom housing. A pressure sensor 50 positioned adjacent the separation surface 35 of the bottom housing 25 and connected by a passageway to the instrument compartment in the bottom housing, wherein the pressure sensor is configured to detect changes of pressure in the bottle enclosure. A computer may be positioned within the instrument compartment and in data communication with the pressure sensor.

At least one audiovisual accessory such as a camera 120 may also positioned proximately to the bottle enclosure 20 and configured to collect environmental sensor data related to the bottle enclosure 20, wherein the audiovisual accessory is in electronic communication with the computer. The audiovisual accessory is selected from the group consisting of a camera, a light sensor, a heat sensor, an alarm function, and a microphone.

Accordingly the feeding bottle 10 may have a mounting device 60 connected to the bottle enclosure 20 for incorporating the audiovisual accessory onto the bottle enclosure and connecting the audiovisual accessory 120 onto the computer. In some embodiments, the audiovisual accessory is a camera and the environmental sensor data comprises images of the feeding bottle in use. The images are analyzed by the computer to recognize an infant's facial expression, readiness to feed, hunger cues, conditions of meal termination, bottle emptying and presence of a caregiver. The computer may be configured to provide output feedback data to caregivers and providers on infant feeding practices, assessments regarding readiness to feed in premature or medically compromised infants, feeding difficulties such as dysfluent or inconsistent sucking patterns, poor sucking strength or stamina, poor coordination with respiration, and status of infants with failure to thrive.

Although the present disclosure has been described in detail with reference to particular arrangements and configurations, these example configurations and arrangements may be changed significantly without departing from the scope of the present disclosure. For example, although the present disclosure has been described with reference to particular communication exchanges involving certain network access and protocols, network device may be applicable in other exchanges or routing protocols. Moreover, although network device has been illustrated with reference to particular elements and operations that facilitate the communication process, these elements, and operations may be replaced by any suitable architecture or process that achieves the intended functionality of network device.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. The structures shown in the accompanying figures are susceptible to 3-D modeling and can be described relative to vertical, longitudinal and lateral axes established with reference to neighboring components as necessary.

Note that in this Specification, references to various features (e.g., elements, structures, modules, components, steps, operations, characteristics, etc.) included in "one embodiment", "example embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments. Note also that an "application" as used herein this Specification, can be inclusive of an executable file comprising instructions that can be understood and processed on a computer, and may further include library modules loaded during execution, object files, system files, hardware logic, software logic, or any other executable modules.

In example implementations, at least some portions of the activities may be implemented in software provisioned on a networking device. In some embodiments, one or more of these features may be implemented in computer hardware, provided external to these elements, or consolidated in any appropriate manner to achieve the intended functionality. The various network elements may include software (or reciprocating software) that can coordinate image development across domains such as time, amplitude, depths, and various classification measures that detect movement across frames of image data and further detect particular objects in the field of view in order to achieve the operations as outlined herein. In still other embodiments, these elements may include any suitable algorithms, hardware, software, components, modules, interfaces, or objects that facilitate the operations thereof. F Furthermore, computer systems described and shown herein (and/or their associated structures) may also include suitable interfaces for receiving, transmitting, and/or otherwise communicating data or information in a network environment. Additionally, some of the processors and memory elements associated with the various nodes may be removed, or otherwise consolidated such that single processor and a single memory element are responsible for certain activities. In a general sense, the arrangements depicted in the Figures may be more logical in their representations, whereas a physical architecture may include various permutations, combinations, and/or hybrids of these elements. It is imperative to note that countless possible design configurations can be used to achieve the operational objectives outlined here. Accordingly, the associated infrastructure has a myriad of substitute arrangements, design choices, device possibilities, hardware configurations, software implementations, equipment options, etc.

In some of example embodiments, one or more memory elements (e.g., memory can store data used for the operations described herein. This includes the memory being able to store instructions (e.g., software, logic, code, etc.) in non-transitory media, such that the instructions are executed to carry out the activities described in this Specification. A processor can execute any type of computer readable instructions associated with the data to achieve the operations detailed herein in this Specification. In one example, processors (e.g., processor) could transform an element or an article (e.g., data) from one state or thing to another state or thing. In another example, the activities outlined herein may be implemented with fixed logic or programmable logic (e.g., software/computer instructions executed by a processor) and the elements identified herein could be some type of a programmable processor, programmable digital logic (e.g., a field programmable gate array (FPGA), an erasable programmable read only memory (EPROM), an electrically erasable programmable read only memory (EEPROM)), an ASIC that includes digital logic, software, code, electronic instructions, flash memory, optical disks, CD-ROMs, DVD ROMs, magnetic or optical cards, other types of machine-readable mediums suitable for storing electronic instructions, or any suitable combination thereof.

These devices may further keep information in any suitable type of non-transitory storage medium (e.g., random access memory (RAM), read only memory (ROM), field programmable gate array (FPGA), erasable programmable read only memory (EPROM), electrically erasable programmable ROM (EEPROM), etc.), software, hardware, or in any other suitable component, device, element, or object where appropriate and based on particular needs. Any of the memory items discussed herein should be construed as being encompassed within the broad term 'memory element.' Similarly, any of the potential processing elements, modules, and machines described in this Specification should be construed as being encompassed within the broad term 'processor.'

Conclusion

Although embodiments have been described in language specific to structural features and/or methodological acts, it is to be understood that the disclosure is not necessarily limited to the specific features or acts described. Rather, the specific features and acts are disclosed herein as illustrative forms of implementing the embodiments.

The invention claimed is:
1. A feeding bottle comprising:
   a bottle enclosure defining a hollow bottle chamber, wherein the enclosure defines a feeding outlet at a first end and an attachment structure at a second end;
   a bottom housing defining an instrument compartment extending between a closed exterior portion of the bottom housing and a separation surface within the bottom housing, wherein the bottom housing is configured for detachable connection to the attachment structure of the bottle enclosure;
   a relief valve positioned within the separation surface of the bottom housing;
   a pressure sensor positioned adjacent the separation surface of the bottom housing and connected by a passageway to the instrument compartment in the bottom housing;
   a liner between the bottle enclosure and the pressure sensor,
   wherein the liner separates fluid in the hollow bottle chamber from the pressure sensor, and the pressure sensor is configured to detect changes of pressure in the bottle enclosure.
2. A feeding bottle according to claim 1, further comprising:
   a computer comprising at least a power source, a processor and memory storing computer implemented soft- ware, wherein the computer is configured to receive pressure data from the pressure sensor.

3. A feeding bottle according to claim 2, wherein the software is configured with computer readable commands that utilize the pressure data and changes in the pressure data to track feeding patterns from the feeding outlet.

4. A feeding bottle according to claim 3, wherein the feeding patterns calculated by the computer comprise at least one of the following: measurements of suck counts, sucking rate and frequency, sucking strength, volume of consumption per suck, and changes in these metrics across a meal and between meals.

5. A feeding bottle according to claim 2, further comprising an accelerometer in electronic communication with the computer to monitor bottle movement and orientation.

6. A feeding bottle according to claim 2 further comprising an alarming function controlled by the computer.

7. A feeding bottle according to claim 2, further comprising a light source configured to direct light from the bottom housing into the hollow bottle chamber and at least one light sensitive sensor connected to the computer within the instrument compartment such that contents of the bottle enclosure can be analyzed for composition by image analysis.

8. A feeding bottle according to claim 7, wherein the light sensitive sensor is configured to measure spectral compositions of light directed to contents of the hollow bottle chamber.

9. A feeding bottle according to claim 1, wherein the fluid in the hollow bottle chamber comprises a nutritional substance within the hollow bottle chamber, wherein the nutritional substance is sufficiently fluidic to move from the hollow bottle chamber through the feeding outlet, creating a change in pressure within the bottle enclosure that is detectable by the pressure sensor.

10. A feeding bottle according to claim 1, wherein the passageway between the pressure sensor and the instrument compartment comprises a tube that provides a reference pressure from the instrument compartment to the pressure sensor.

11. A feeding bottle according to claim 10, wherein the reference pressure is atmospheric pressure within the instrument compartment, and wherein a change in pressure within the bottle enclosure is determined by comparison to the atmospheric pressure.

12. A feeding bottle comprising:
a bottle enclosure defining a feeding outlet at a first end and an attachment structure at a second end;
a bottom housing defining an instrument compartment extending between a closed exterior portion of the bottom housing and a separation surface within the bottom housing, wherein the bottom housing is configured for detachable connection to the attachment structure of the bottle enclosure;
a computer within the instrument compartment comprising at least a processor and memory storing computer executable software therein;
a relief valve positioned within the separation surface of the bottom housing;
a pressure sensor positioned adjacent the separation surface of the bottom housing and connected by a passageway to the instrument compartment in the bottom housing;
a liner between the bottle enclosure and the pressure sensor, wherein the liner separates the pressure sensor from a fluid in the bottle enclosure;
at least one actuator controlled by the computer and connected to the bottle enclosure to control a rate of fluid discharge at the feeding outlet according to the software;
wherein the pressure sensor is configured to detect changes of pressure in the bottle enclosure for synchronizing the rate of fluid discharge produced by the actuator.

13. A feeding bottle according to claim 12, wherein the actuator is controlled by the software to expel a calculated volume of fluid discharge from the feeding outlet.

14. A feeding bottle system comprising:
a bottle enclosure defining a hollow bottle chamber, wherein the enclosure defines a feeding outlet at a first end and an attachment structure at a second end;
a bottom housing defining an instrument compartment extending between a closed exterior portion of the bottom housing and a separation surface within the bottom housing, wherein the bottom housing is configured for detachable connection to the attachment structure of the bottle enclosure;
a relief valve positioned within the separation surface of the bottom housing;
a pressure sensor positioned adjacent the separation surface of the bottom housing and connected by a passageway to the instrument compartment in the bottom housing, wherein the pressure sensor is configured to detect changes of pressure in the bottle enclosure;
a liner between the bottle enclosure and the pressure sensor;
wherein the liner separates fluid in the hollow bottle chamber from the pressure sensor, and the pressure sensor is configured to detect changes of pressure in the bottle enclosure;
a computer positioned within the instrument compartment and in data communication with the pressure sensor;
at least one audiovisual accessory positioned proximately to the bottle enclosure and configured to collect environmental sensor data related to the bottle enclosure, wherein the audiovisual accessory is in electronic communication with the computer.

15. A feeding bottle system according to claim 14, wherein the audiovisual accessory is selected from the group consisting of a camera, a light sensor, a heat sensor, an alarm function, and a microphone.

16. A feeding bottle system according to claim 15, further comprising a mounting connected to the bottle enclosure for incorporating the audiovisual accessory onto the bottle enclosure and connecting the audiovisual accessory to the computer.

17. A feeding bottle system according to claim 16, further comprising a regulatory vacuum device connected to the computer to deliver a specific volume of nutritional fluid from the hollow bottle chamber in accordance with the changes of pressure in the bottle enclosure.

* * * * *